United States Patent

Shimizu et al.

[11] Patent Number: 5,968,030
[45] Date of Patent: Oct. 19, 1999

[54] MECHANICAL FASTENING SYSTEM FOR DISPOSABLE ARTICLES

[75] Inventors: Shingo Shimizu; Yoshitaka Mishima, both of Kagawa-ken, Japan

[73] Assignee: Uni-Charm Corporation, Ehime-ken, Japan

[21] Appl. No.: 08/893,715

[22] Filed: Jul. 11, 1997

[30] Foreign Application Priority Data

Jul. 12, 1996 [JP] Japan ................................. 8-183808

[51] Int. Cl.6 .................................................. A61F 13/15
[52] U.S. Cl. ........................ 604/390; 604/389; 604/391; 604/385.1
[58] Field of Search ................................. 604/391, 389, 604/390, 386

[56] References Cited

U.S. PATENT DOCUMENTS

| | | | |
|---|---|---|---|
| 4,650,082 | 3/1987 | Paciorek | 215/230 |
| 4,680,030 | 7/1987 | Coates et al. | 604/391 |
| 4,869,724 | 9/1989 | Scripps . | |
| 4,917,929 | 4/1990 | Heinecke | 428/41 |
| 4,973,326 | 11/1990 | Wood et al. | 604/391 |
| 5,019,065 | 5/1991 | Scripps | 604/385.1 |
| 5,053,028 | 10/1991 | Zoia et al. | 604/385.1 |
| 5,279,604 | 1/1994 | Robertson et al. | 604/389 |
| 5,549,591 | 8/1996 | Landvogt | 604/389 |
| 5,611,789 | 3/1997 | Seth | 604/391 |
| 5,860,964 | 1/1999 | Willekens et al. | 604/389 |

FOREIGN PATENT DOCUMENTS

| | | |
|---|---|---|
| 985452 | 3/1976 | Canada . |
| 0 182 692 | 5/1986 | European Pat. Off. . |
| 0 529 681 | 3/1993 | European Pat. Off. . |
| 296 16 711 | 11/1996 | Germany . |

*Primary Examiner*—John G. Weiss
*Assistant Examiner*—Joseph F. Weiss, Jr.
*Attorney, Agent, or Firm*—Lowe Hauptman Gopstein Gilman & Berner

[57] ABSTRACT

A disposable diaper provided with a pair of tape fasteners each having a proximal end section secured to a side portion of a rear waist region of the diaper and a distal end section folded back onto an inner surface of the diaper, a part of the distal end section is releasably welded to the inner surface of the diaper and thereby to facilitate handling of the diaper when it is put on the wearer.

14 Claims, 2 Drawing Sheets

MECHANICAL FASTENING SYSTEM FOR DISPOSABLE ARTICLES

BACKGROUND OF THE INVENTION

This invention relates generally to disposable diapers provided with tape fasteners at transversely opposite side edges thereof respectively.

It is well known to employ a pair of tape fasteners extending outward from transversely opposite side edges of a rear waist region of a disposable diaper, respectively, and adapted to be releasably anchored on a front waist region of the diaper at predetermined positions for reliably putting the diaper on the wearer. It is also well known to adopt one of paired hook/loop members forming together a so-called mechanical fastener. For example, U.S. Pat. No. 4,869,724 discloses a disposable diaper provided with a pair of tape fasteners extending outward from transversely opposite side edges of a rear waist region of the diaper, respectively, and including hook-shaped fastening elements. When the diaper is put on the wearer, these hook-shaped fastening elements are anchored on landing zones formed on an outer surface of a front waist region of the diaper.

However, with the known disposable diapers as have been described above, the tape fasteners remain extended from the transversely opposite side edges of the rear waist region of the diaper and the hook-shaped fastening elements are exposed before the diaper is put on the wearer. In consequence, these fastening elements are apt to catch various things therearound, for example, when a plurality of diapers must be put in order, and the mother is burdened with a troublesome labor. To avoid an obstruction by the presence of such tape fasteners, an inner surface of the diaper may be provided with cooperating fastener members on which the tape fasteners could be temporarily anchored. However, such measure will be inevitably accompanied with a significant increase of manufacturing cost.

SUMMARY OF THE INVENTION

In view of the problem as has been described above, it is a principal object of the invention to provide a tape fastener adopting the mechanical fastener improved by a relatively simple measure so that handling of disposable diapers might not be obstructed by the presence of the tape fastener.

The object set forth above is achieved, according to the invention, by a disposable diaper comprising a liquid-permeable topsheet, a liquid-impermeable backsheet and a liquid-absorbent core disposed therebetween which form a front waist region, a rear waist region and a crotch region extending therebetween. One of the front and rear waist regions is provided with a pair of tape fasteners extending outward from transversely opposite side edges of that waist region so as to be releasably anchored on the other waist region at predeterminded positions:

At least a portion of an inner surface of said disposable diaper extending in the proximity of a proximal end section of said tape fastener and/or at least a portion of an inner surface of said tape fastener is or are made of thermally meltable material. The tape fastener is folded back, with the inner surface of said tape fastener inside, onto the inner surface of said diaper in the proximity of said proximal end section; and the inner surface of said diaper in the proximity of said proximal end section is releasably welded to the inner surface of said tape fastener at said portion or portions made of thermally meltable material.

The disposable diaper according to the invention allows the user to handle the diaper without being obstructed by the presence of the tape fasteners, since the tape fasteners adopting the mechanical fasteners are folded back onto the inner surface of the diaper and releasably welded the inner surface before the diaper is put on the wearer.

In general, hook-shaped elements forming the fastening zone of the tape fastener can be temporarily anchored on the topsheet made of a nonwoven fabric and thereby achieve the same purpose as the invention as long as a forward end of each hook-shaped element is adequately sharp. However, when the forward end of the hook-shaped element is blunted in order to prevent such sharp forward end of the hook-like element from irritating the wearer's skin, the temporary anchoring of the hook fastener on the topsheet is not possible. The disposable diaper according to the invention overcomes this problem and effectively achieves the desired temporary anchoring using a unique tape fastener having no apprehension that the fastener elements might irritate the wearer's skin.

Other and further objects, features and advantages of the invention will appear more fully from the following description.

DESCRIPTION OF THE PREFERRED EMBODIMENT

Figure 1:
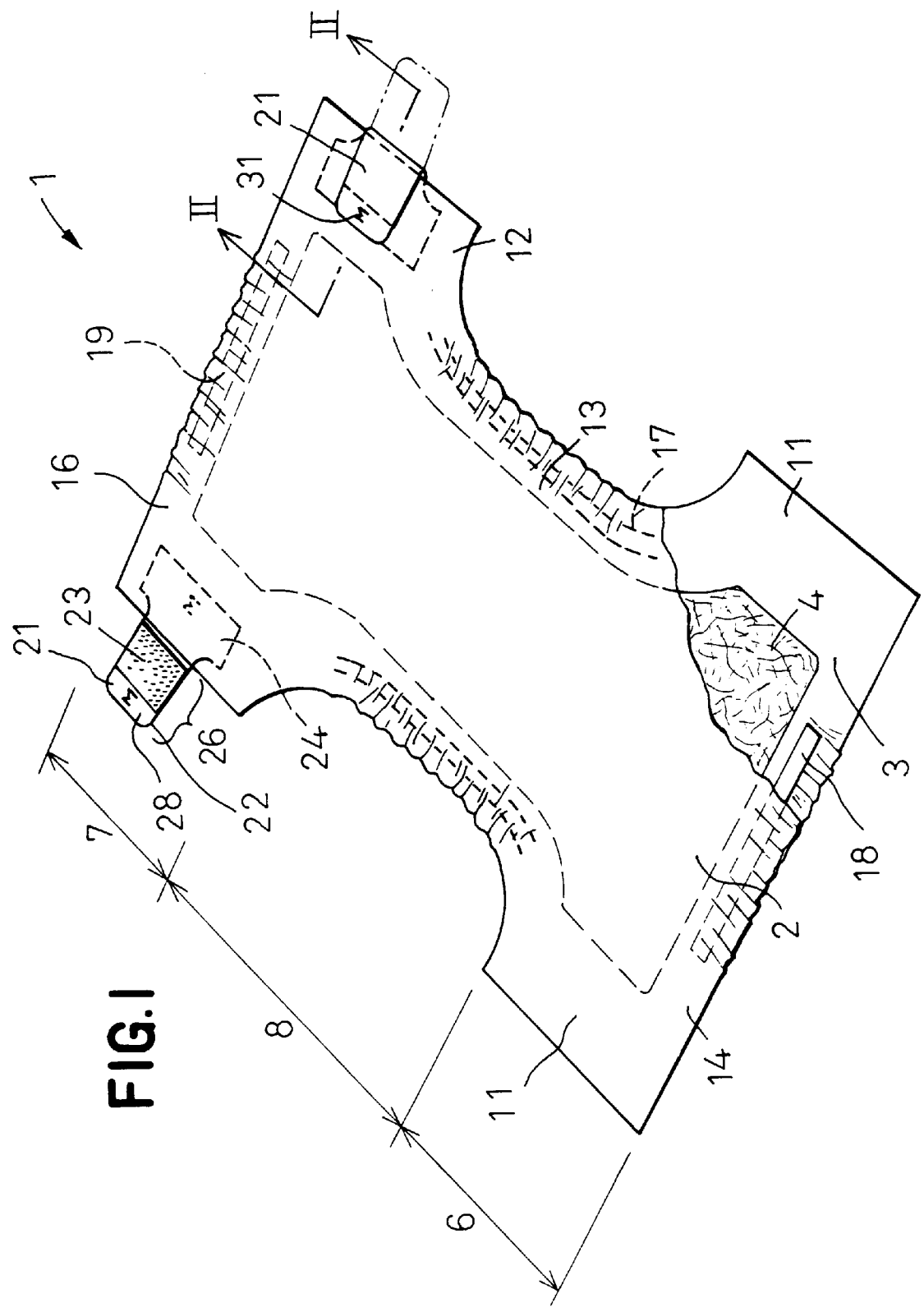
FIG. 1 is a perspective view of a disposable diaper according to the invention as partially broken way.

Disposable diaper 1 shown by FIG. 1 in a perspective view as partially broken away comprises a liquid-permeable topsheet 2, a liquid-impermeable backsheet 3 and a liquid-absorbent core 4 that form a front waist region 6, a rear waist region 7 and a crotch region 8 extending between these two waist regions 6, 7 as viewed in the longitudinal direction. The topsheet 2 and the backsheet 3 are bonded to each other along their portions extending outward beyond a peripheral edge of the absorbent core 4 to define transversely opposite side edges 11, 12 of the front and rear waist regions 6, 7, respectively, transversely opposite side edges 13 of the crotch region 8 defining respective leg-openings and longitudinally opposite ends 14, 16 of the front waist region 6 and the rear waist region 7, respectively, defining together a waist-opening. The transversely opposite side edges 13 and the longitudinally opposite ends 14, 16 are provided with leg-openings elastic members 17 and waist-opening elastic members 18, 19. These elastic members 17, 18, 19 are secured in their longitudinally extended conditions between the topsheet 2 and the backsheet 3. The rear waist region 7 is provided on its transversely opposite side edges 12 with laterally extendible tape fasteners 21, respectively. These tape fasteners 21 are shown as one of them is folded back onto an inner side of the diaper 1 and the other is unfolded outward.

In the diaper 1, the topsheet 2 is formed by a nonwoven fabric or a perforated film of thermally meltable synthetic resin such as polypropylene and the backsheet 3 is formed by a film of thermally meltable synthetic resin such as polyethylene and polypropylene. The tape fastener 21 comprises a base tape 22 made of a nonwoven fabric and/or a film obtained from thermally meltable synthetic resin such as polypropylene and an fastening zone 23 formed on an inner surface of the base tape 22. A proximal end section 24 of the tape fastener 21 is secured to the side edge 12 of the diaper 1 and a distal end section 26 of the tape fastener is extendible from the side edge 12. The fastening section 23 is formed on the inner surface of the distal end section 26 and a tab 28 of the tape fastener 21 is defined by an outer extension of the fastening zone 23.

Figure 2:
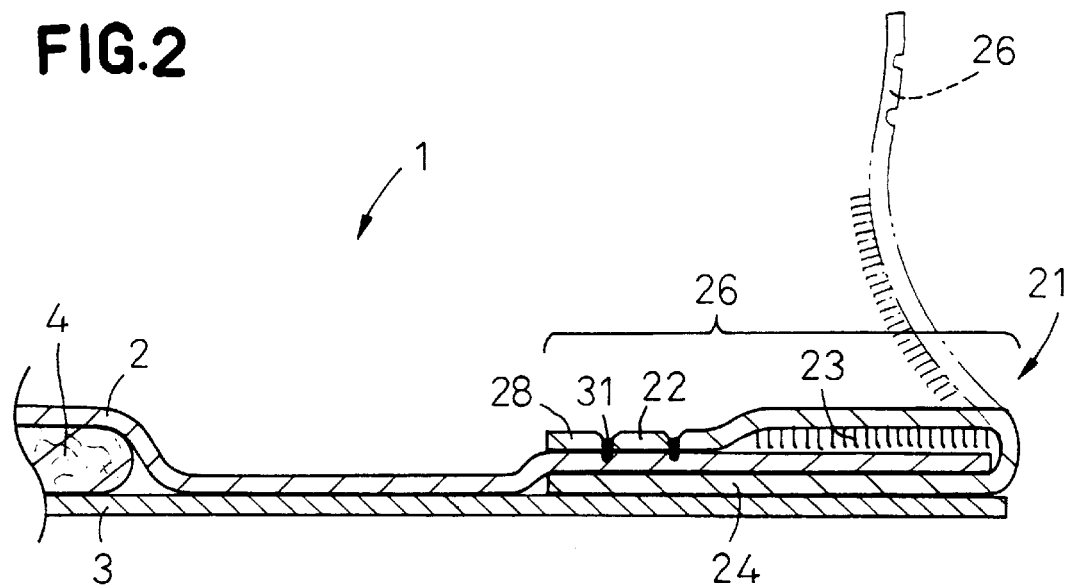
FIG. 2 is a sectional view taken along line II—II in FIG. 1.

FIG. 2 is a sectional view taken along line II—II in FIG. 1. The tape fastener 21 has the proximal end section 24 bonded to respective inner surfaces of the topsheet 2 and the backsheet 3 by means of hot melt adhesive (not shown) and the distal end section 26 is folded back onto the outer surface of the topsheet 2. The tab 28 forming a part of the base tape 22 has one to three extremely narrow zones 31 at which the tab 28 is releasably welded to the topsheet 2. Each of these narrow zones 31 provided for such welding has an area of 0.3–2.0 $mm^2$. In the illustrated embodiment, the welded zone 31 describes a small M on the tab 28. The fastening zone 23 is formed by bonding a hook member of the mechanical fastener well known, for example, under the trademark VELCRO comprising hook/loop fastening members to the inner surface of the distal end section 26 by suitable means (not shown) such as the well known welding technique.

According to the arrangement as has been described above, the tape fastener 21 may be pulled upward with the tab 28 held between the user's fingers from the inner surface of the diaper 1 (i.e., the outer surface of the topsheet 2) and thereby to separate the distal end section 26 of the tape fastener 21 from the inner surface of the diaper 1 at the welded zone 31. In this way, the tape fastener 21 becomes ready to be used as indicated by imaginary lines. Such separation of the tape fastener 21 from the inner surface of the diaper 1 is achieved by peel-off of the welded zone 31 from the topsheet 2 or tear-off of the topsheet 2 at the welded zone 31.

Figure 3:
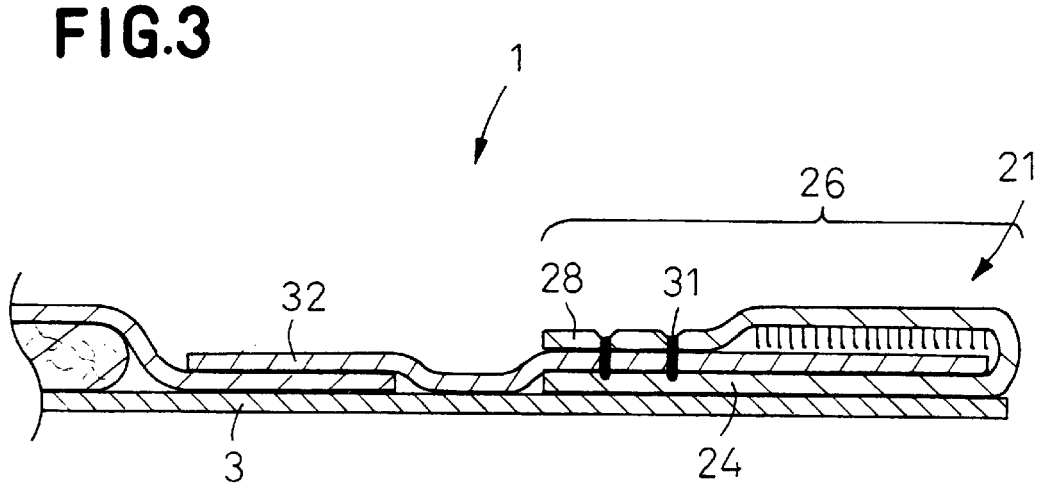
FIG. 3 is a view similar to FIG. 2 but showing an alternative embodiment of the invention.

FIG. 3 is a view similar to FIG. 2 but showing an alternative embodiment of the invention. According to this embodiment of the diaper 1, the topsheet 2 has a width narrower than a width of the backsheet 3 and a portion of the backsheet 3 extending outward beyond a side edge of the topsheet 2 is covered with a second topsheet 32. These two sheets 3, 32 are bonded to each other by means of hot melt adhesive (not shown). The tape fastener 21 has the proximal end section 24 bonded to the respective inner surfaces of the second topsheet 32 and the backsheet 3, on one hand, and the tab 28, the second topsheet 32 and the proximal end section 24 welded together in the welded zone 31. According to this alternative embodiment also, the tape fastener 21 may be pulled upward with the tab 28 held between the user's fingers and easily separated from the inner surface of the diaper 1 (i.e., the outer surface of the second topsheet 32). With the diaper 1 having such tape fastener constructed in accordance with this alternative embodiment, a damage possibly occurring on the inner side of the diaper for separation of the tape fastener 21 can be alleviated by use of the second topsheet 32 having a tear strength higher than that of the topsheet 2. Additionally, a compatibility of the topsheet with the tape fastener 21 regarding the thermal meltabilities of these two components can be easily improved by use of the second topsheet 32 having a thermal meltability different from that of the topsheet 2. For example, the second topsheet 32 made of material having a melting point higher than that of the base tape 22 of the tape fastener 21 may be used to alleviate a deterioration possibly occurring in a surface smoothness of the second topsheet 32 in the welded zone 31.

With the diaper 1 according to the invention, it is necessary and sufficient for both the tape fastener 21 and the topsheet 2 (or the second topsheet 32) of the diaper 1 that these two components are thermally meltable in their zones corresponding to the welded zone 31 and in the proximity of these zones. Such requirement is met also by covering the inner surface of the diaper 1 over an area occupied by the proximal end section 24 of the tape fastener 21 and a zone extending in the proximity of this area with a sheet having a desired thermal meltability. Alternatively, the proximal end section 24 may be exposed in the inner surface of the diaper 1 and the distal end section 26 may be directly welded thereto. It is also possible within the scope of the invention to melt one of the inner surface of the diaper 1 and the distal end section 26 and then to bond this to the other which is not molten. To weld the distal end section 26 to the inner surface of the diaper 1, a suitable technique such as the well known thermal embossing or ultrasonic welding may be used.

Having described our invention as related to the embodiments shown in the accompanying drawings, it is our intention that the invention be not limited by any of the details of description, unless otherwise specified, but rather be construed broadly within its spirit and scope as set out in the accompanying claims.

What is claimed is:

1. A disposable diaper comprising a liquid-permeable topsheet, a liquid-impermeable backsheet and a liquid-absorbent core disposed therebetween which form a front waist region, a rear waist region and a crotch region extending therebetween, one of said front and rear waist regions being provided with a pair of tape fasteners extending outward from transversely opposite side edges of said one waist region so as to be releasably anchored on the other waist region at predetermined positions, wherein:

at least one of (1) a portion of an inner surface of said disposable diaper extending in the proximity of a proximal end section of said tape fastener and (2) at least a portion of an inner surface of said tape fastener include(s) thermally meltable material; said tape fastener being folded back so that the inner surface of a distal end section of said tape fastener contacts the inner surface of said diaper in the proximity of said proximal end portion; and the inner surface of said diaper in the proximity of said proximal end portion is releasably welded to the inner surface of the distal end section of said tape fastener at said portion(s) made of thermally meltable material.

2. The disposable diaper according to claim 1, wherein said topsheet is made of thermally meltable material and extends outward beyond a side edge of said absorbent core together with said backsheet; said topsheet defines the inner surface of said diaper extending in the proximity of said proximal end section; portions of said topsheet and said backsheet extending outward beyond the side edge of said absorbent core being bonded to each other; said proximal end section of said tape fastener being positioned between the extending portions of said topsheet and said backsheet while said distal end section of said tape fastener is folded back onto the inner surface of said topsheet to overlie said proximal end portion; and an outer surface of said topsheet is releasably welded to the inner surface of the distal end section of said tape fastener.

3. The disposable diaper according to claim 1, wherein said topsheet is made of thermally meltable material and has a width narrower than a width of the backsheet and extends outward beyond a side edge of said absorbent core and a portion of said backsheet extends outward beyond a side edge of said topsheet and is covered with a second topsheet made of thermally meltable material, wherein said second topsheet defines the inner surface of said diaper extending in the proximity of said proximal end section; portions of said topsheet and said backsheet extending outward beyond the side edge of said absorbent core as well as the portion of said backsheet extending outward beyond the side edge of said topsheet and said second topsheet are bonded to each other, respectively; said proximal end section of said tape fastener is positioned between the extending portion of said backsheet and said second topsheet and the distal end section of said tape fastener is folded back onto an inner surface of said topsheet in the proximity of said proximal end portion; and an outer surface of said second topsheet is releasably welded to the inner surface of the distal end section of said tape fastener.

4. The disposable diaper according to claim 3, wherein said second topsheet has a tear strength greater than that of the topsheet.

5. The disposable diaper according to claim 3, wherein said second topsheet has a thermal meltability different than that of the topsheet.

6. The disposable diaper according to claim 3, wherein said second topsheet is made of a material having a melting point greater than that of the tape fastener.

7. The disposable diaper according to claim 1, wherein said tape fastener further comprises a tab forming a forward end of said distal end section, and said tab is releasably welded to the inner surface of said diaper.

8. The disposable diaper according to claim 7, wherein the releasable weld is formed as a plurality of narrow welded zones.

9. The disposable diaper according to claim 8, wherein said narrow welded zones are formed inwardly of portions of said tape fasteners adapted to be releasably anchored on the other waist region when the associated tape fastener is releasably welded to the diaper.

10. The disposable diaper according to claim 8, wherein said narrow welded zones are located only in a central portion of the tab.

11. The disposable diaper according to claim 8, wherein said releasable weld is located only at the distal end section of the tape fastener.

12. The disposable diaper according to claim 1, wherein said releasable weld is located only at the distal end section of the tape fastener.

13. The disposable diaper according to claim 1, wherein the inner surface of said diaper includes said proximal end portion and said distal end is releasably welded to said proximal end portion.

14. The disposable diaper according to claim 1, wherein the releasable weld between the tape fastener and the diaper is formed only along a portion of the periphery of a fastening portion of the tape fastener concealed between the inner surfaces of the tape fastener and the diaper.

* * * * *